(12) United States Patent
Marteau et al.

(10) Patent No.: US 9,532,768 B2
(45) Date of Patent: *Jan. 3, 2017

(54) MULTI-HEADED IMAGING PROBE AND IMAGING SYSTEM USING SAME

(71) Applicant: General Electric Company, Schenectady, NY (US)

(72) Inventors: Jean-Michel Marteau, Asnieres sur Seine (FR); Aurelie Roncaglioni, Bois d'Arcy (FR); Lionel Wodecki, Maisons-Alfort (FR)

(73) Assignee: General Electric Company, Schenectady, NY (US)

( * ) Notice: Subject to any disclaimer, the term of this patent is extended or adjusted under 35 U.S.C. 154(b) by 327 days.

This patent is subject to a terminal disclaimer.

(21) Appl. No.: 13/913,124

(22) Filed: Jun. 7, 2013

(65) Prior Publication Data

US 2014/0364730 A1 Dec. 11, 2014

Related U.S. Application Data

(63) Continuation of application No. 13/281,283, filed on Oct. 25, 2011, now Pat. No. 8,480,591, which is a
(Continued)

(51) Int. Cl.
*A61B 8/00* (2006.01)
*A61B 8/08* (2006.01)

(52) U.S. Cl.
CPC ........... *A61B 8/4477* (2013.01); *A61B 8/4209* (2013.01); *A61B 8/483* (2013.01); *A61B 8/54* (2013.01);
(Continued)

(58) Field of Classification Search
CPC ......... A61B 8/00; A61B 8/463; A61B 8/4427; A61B 8/44; A61B 8/4477; A61B 8/4209; A61B 8/483; A61B 8/54; G01S 7/52079
(Continued)

(56) References Cited

U.S. PATENT DOCUMENTS 5,186,176 A 2/1993 Hiki et al.
5,505,203 A 4/1996 Deitrich et al.
(Continued)

FOREIGN PATENT DOCUMENTS

EP 0 919 189 A1 6/1999
EP 0 919 987 A2 6/1999
(Continued)

OTHER PUBLICATIONS

Machine translation of JP 2001-299754.*

*Primary Examiner* — Christopher Cook
*Assistant Examiner* — Carolyn Pehlke
(74) *Attorney, Agent, or Firm* — Dean D. Small; The Small Patent Law Group, LLC

(57) ABSTRACT

A diagnostic imaging system is provided that includes an image acquisition component, a transmitter operatively coupled to the image acquisition component to transmit a signal therefrom, and a beamformer operatively coupled to the image acquisition component to receive image data therefrom. Also included is a processor configured to assemble images from the acquired image data and a display configured to display the images. The image acquisition component includes a multi-headed probe that has a plurality of transducers configured to permit a change of active transducers during an imaging session without a change of the image acquisition component.

29 Claims, 11 Drawing Sheets

Related U.S. Application Data continuation of application No. 11/893,734, filed on Aug. 17, 2007, now Pat. No. 8,043,221.

(52) U.S. Cl.
CPC ............ *A61B 8/4405* (2013.01); *A61B 8/4427* (2013.01); *A61B 8/4455* (2013.01); *A61B 8/4472* (2013.01); *A61B 8/4494* (2013.01); *A61B 8/463* (2013.01); *A61B 8/466* (2013.01); *A61B 8/469* (2013.01)

(58) Field of Classification Search
USPC ......... 600/437, 440, 446, 453–459; 367/153, 367/155; 73/596, 584, 609, 618, 628
See application file for complete search history.

(56) References Cited

U.S. PATENT DOCUMENTS

| | | | |
|---|---|---|---|
| 5,617,866 A | 4/1997 | Marian, Jr. | |
| 6,117,085 A | 9/2000 | Picatti et al. | |
| 6,142,946 A | 11/2000 | Hwang et al. | |
| 6,423,002 B1 | 7/2002 | Hossack | |
| 7,303,530 B2 | 12/2007 | Barnes et al. | |
| 2004/0236223 A1 | 11/2004 | Barnes et al. | |
| 2005/0113700 A1 | 5/2005 | Yanagihara et al. | |
| 2005/0165312 A1 | 7/2005 | Knowles et al. | |
| 2005/0240125 A1 | 10/2005 | Makin et al. | |
| 2007/0016058 A1 | 1/2007 | Kerwin | |
| 2008/0114253 A1 | 5/2008 | Randall et al. | |

FOREIGN PATENT DOCUMENTS

| | | |
|---|---|---|
| JP | 63-032508 U1 | 3/1988 |
| JP | 01-293847 A | 11/1989 |
| JP | 02-082314 U1 | 6/1990 |
| JP | 03-106352 A | 5/1991 |
| JP | 04-285546 A | 10/1992 |
| JP | 11-221211 A | 8/1999 |
| JP | 2001-299754 | 10/2001 |
| JP | 2004-187880 | 7/2004 |
| WO | WO 2004/073892 A1 | 9/2004 |

\* cited by examiner

MULTI-HEADED IMAGING PROBE AND IMAGING SYSTEM USING SAME

CROSS REFERENCE TO RELATED APPLICATIONS

This application is a Continuation of U.S. patent application Ser. No. 13/281,283 entitled "MULTI-HEADED IMAGING PROBE AND IMAGING SYSTEM USING SAME" filed Oct. 25, 2011 (now U.S. Pat. No. 8,480,591), which is a Continuation of and claims priority to U.S. patent application Ser. No. 11/893,734 entitled "MULTI-HEADED IMAGING PROBE AND IMAGING SYSTEM USING SAME" filed Aug. 17, 2007, now U.S. Pat. No. 8,043,221, both of which are incorporated herein by reference in their entirety.

BACKGROUND OF THE INVENTION

Diagnostic imaging, and in particular, medical imaging may use different imaging modalities to scan a patient or region of interest. For example, to perform an echography, a probe or transducer is placed in contact with a patient's skin. Different probe geometries can be used during an examination to optimize acquisition of images. However, using known ultrasound examination systems, a sonographer must perform additional actions to change a probe during or between patient examinations to use different probe geometries. The time and effort required to change probes can cause physical stress for the sonographer or patient and affect the duration of a patient exam. To reduce these issues, additional connectors could be provided for each of the probes having different geometries. However, providing additional connectors increases the size and portability of the probes, which in many applications is undesirable.

BRIEF DESCRIPTION OF THE INVENTION

In accordance with an embodiment of the present invention, a diagnostic imaging system is provided that includes an image acquisition component, a transmitter operatively coupled to the image acquisition component to transmit a signal therefrom, and a beamformer operatively coupled to the image acquisition component to receive image data therefrom. Also included is a processor configured to assemble images from the acquired image data and a display configured to display the images. The image acquisition component includes a multi-headed probe that has a plurality of transducers configured to permit a change of active transducers during an imaging session without a change of the image acquisition component.

In accordance with another embodiment of the present invention, an image acquisition device for an imaging apparatus is provided. The imaging acquisition device includes a multi-headed probe having plurality of transducers each configured to provide a distinct and different function.

In accordance with yet another embodiment of the present invention, a method for obtaining ultrasound images of a patient is provided. The method uses an ultrasound imaging system that has an image acquisition component encased in a disk-shaped case, a transmitter operatively coupled to the image acquisition component to transmit a signal therefrom, a beamformer operatively coupled to the image acquisition component to receive image data therefrom, a processor configured to assemble images from the image data, and a display configured to display the images. The image acquisition component includes a multi-headed probe that has a plurality of transducers configured to permit a change of active transducers during an imaging session without a change of image acquisition component. The method includes pressing a first window of the disk-shaped case corresponding to a first transducer of the multi-headed probe against the skin of the patient and rocking the disk-shaped case back and forth on the patient's body during the examination. The method further includes rotating the disk-shaped case to select a second window of the disk-shaped case corresponding to a second transducer of the multi-headed probe, and pressing and rocking the second window of the disk-shaped case against the patient's body during the examination.

DETAILED DESCRIPTION OF THE INVENTION

Figure 1:
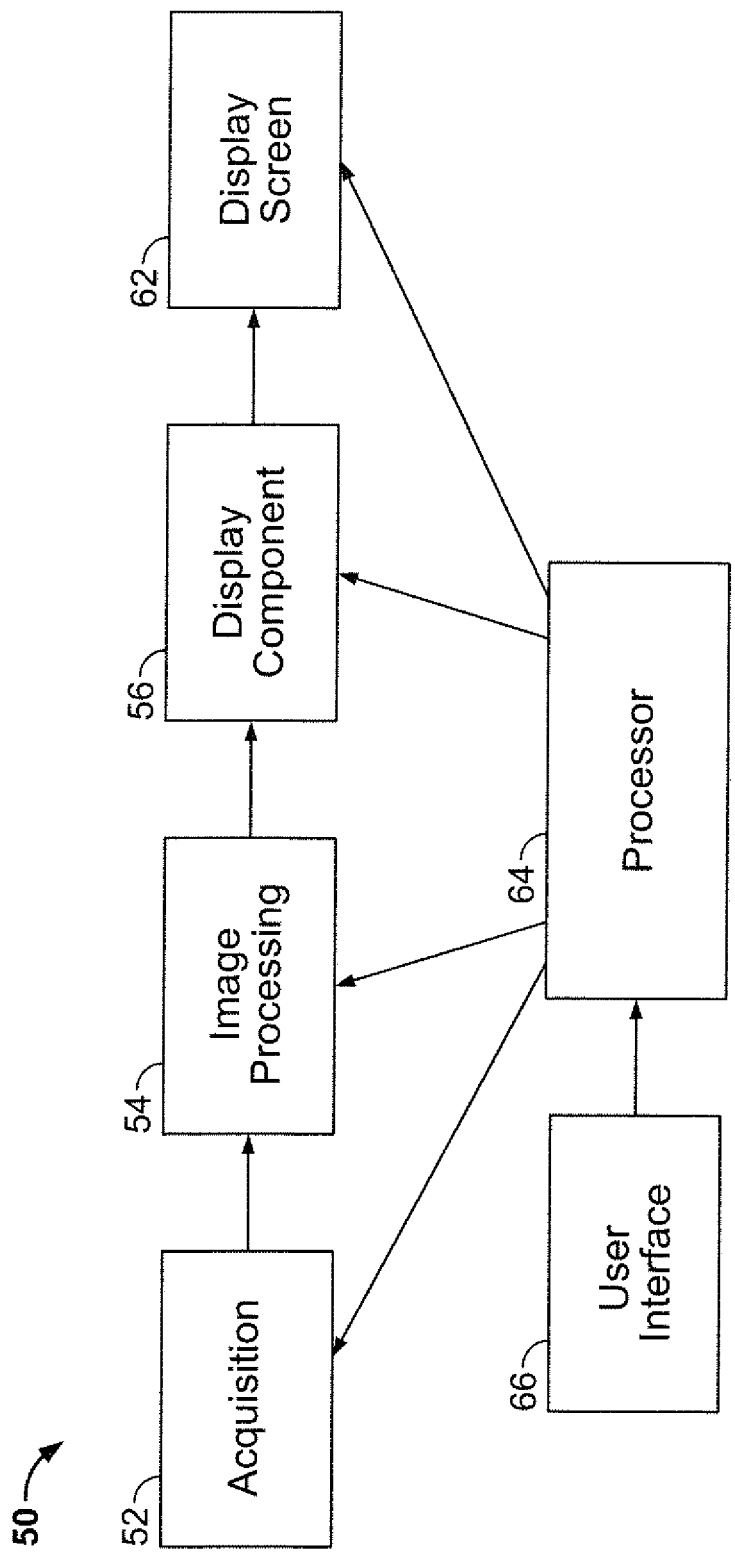
FIG. 1 is a block diagram of a diagnostic imaging system constructed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments of the invention provide a diagnostic imaging system 50 as shown in FIG. 1s. The diagnostic imaging system 50 may be any type of system that uses a hand-held image acquisition component 52. Imaging system 50 is, for example, an ultrasound imaging system or a multi-modal imaging system. However, the various embodiment are not limited to medical imaging systems or imaging systems for imaging human subjects, but may include non-medical systems for imaging non-human objects and for performing non-destructive imaging or testing or security imaging (e.g., airport security screening), etc.

The diagnostic imaging system 50 includes an acquisition component 52 configured to acquire image data (e.g., ultrasound image data). The acquisition component 52 in embodiments of the present invention is, and is hereafter referred to as a multi-headed probe 52 for scanning or otherwise imaging an object or volume of interest. A "multi-headed probe" is a single probe that includes a plurality of transducers, each of which is physically separate from one another (and thus comprising a separate "head") that can be separately operated. For example, one or more transducers are included on a single multi-headed probe 52. The multi-headed probe 52 is operatively connected to an image processing component 54. The image processing component 54 is any type of image processor capable of processing image data acquired using any of the plurality of transducers. Image processing component 54 is also operatively coupled to a display component 56. The display component 56, which may be a controller, configures or formats the processed image data for display on a display screen 62. The display screen 62 may be any type of screen capable of displaying images, graphics, text, etc. For example, the display screen 62 may be a cathode ray tube (CRT) screen, a liquid crystal display (LCD) screen or a plasma screen, among others.

A processor 64 (e.g., computer) or other processing unit controls the various operations within the diagnostic imaging system 50. For example, the processor 64 may receive user inputs from a user interface 66 and display requested image data or adjust the settings for the displayed image data. For example, a user may provide inputs or settings to change the image displayed or the display properties of the display screen 62.

Figure 2:
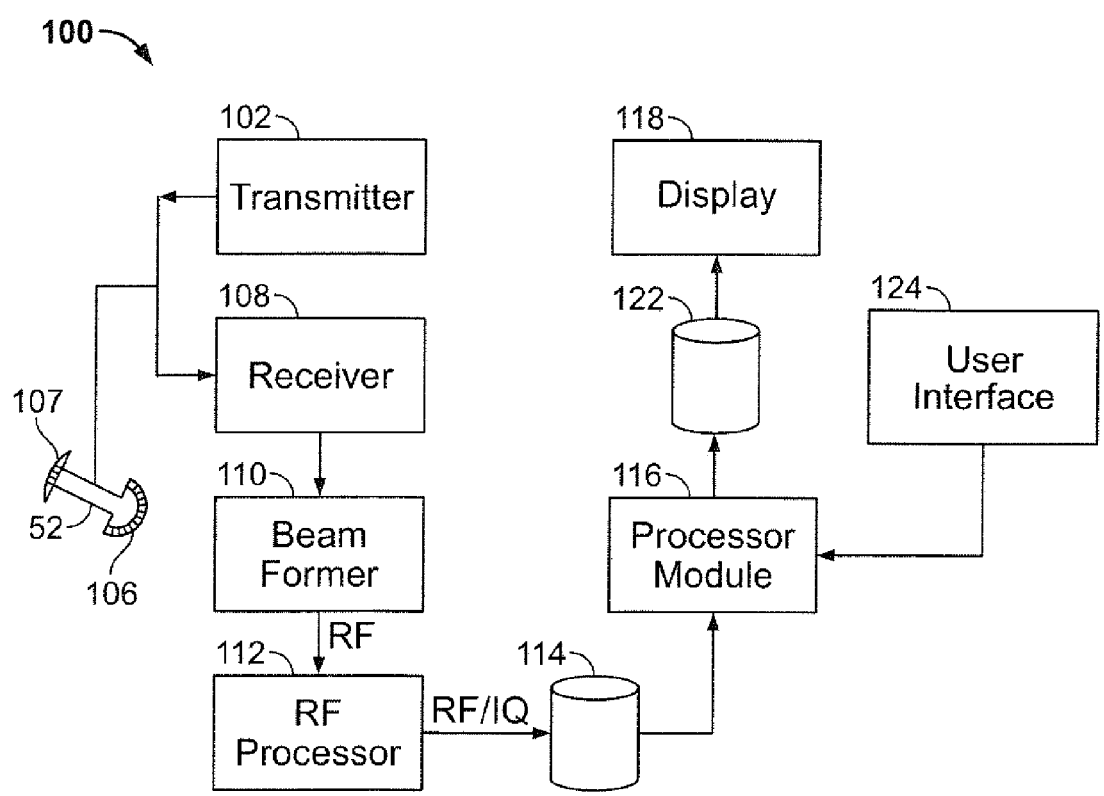
FIG. 2 is a block diagram of an ultrasound imaging system constructed in accordance with an embodiment of the invention.

In some embodiments, the diagnostic imaging system 50 is an ultrasound system 100, such as is shown in the schematic block diagram in FIG. 2. The ultrasound system 100 includes one or more transmitters 102 that drive arrays of elements 104 (e.g., piezoelectric elements) within a selected transducer 106, 107 of multi-headed probe 52 to emit pulsed ultrasonic signals into a body. A variety of geometries may be used. The ultrasonic signals are backscattered from structures in the body, like blood cells or muscular tissue, to produce echoes that return to the elements 104 of the selected transducer 106, 107. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and the processed and displayed in off-line operation.

The processor module 116 is connected to a user interface 124 that may control operation of the processor module 116 as explained below in more detail. The display 118 includes one or more monitors that present patient information, including diagnostic ultrasound images to the user for diagnosis and analysis. One or both of memory 114 and memory 122 may store three-dimensional data sets of the ultrasound data, where such 3-D data sets are accessed to present 2-D and 3-D images. The images may be modified and the display settings of the display 118 also manually adjusted using the user interface 124.

The system 100 may obtain volumetric data sets by various techniques (e.g., 3D scanning, real-time 3D imaging, volume scanning, 2D scanning with transducers having positioning sensors, freehand scanning using a Voxel correlation technique, 2D or matrix array transducers and the like). Transducer 106 or 107 is moved, such as along a linear or arcuate path, while scanning a region of interest (ROI). At each linear or arcuate position, the transducer 106 or 107 obtains scan planes that are stored in the memory 114.

Figure 3:
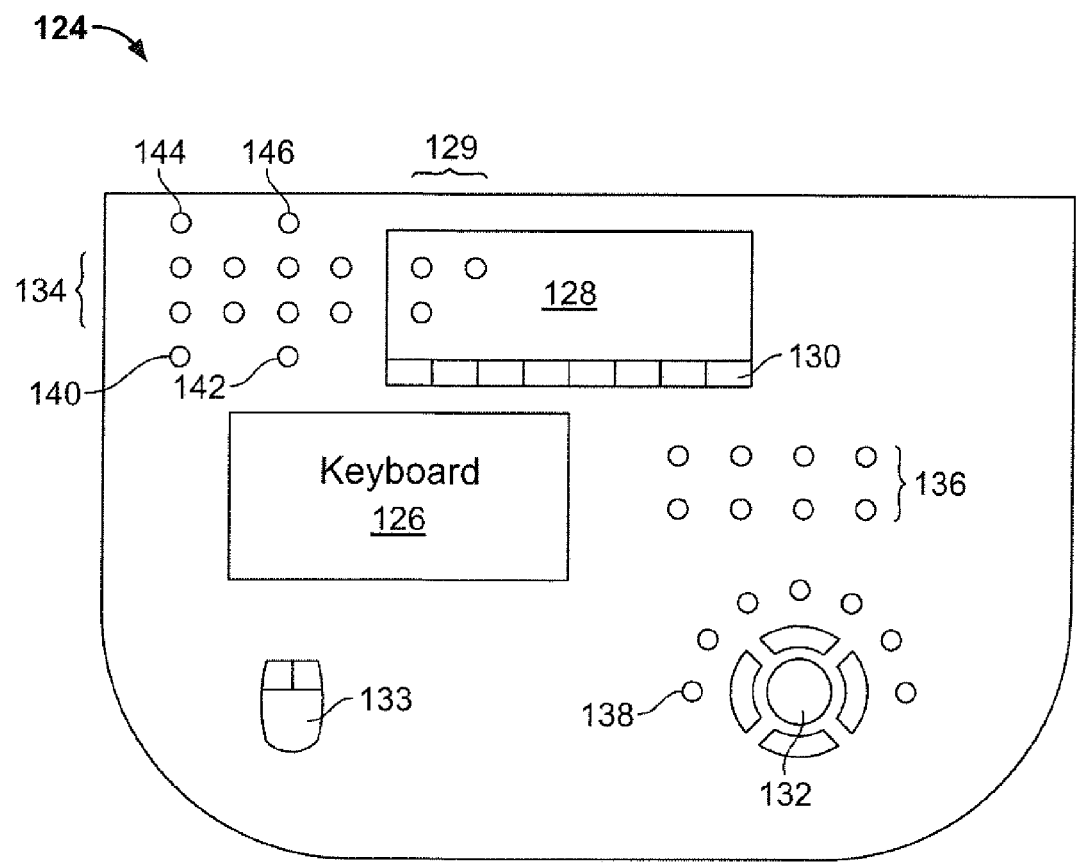
FIG. 3 is a top plan view of a user interface constructed in accordance with an embodiment of the present invention.

FIG. 3 illustrates the user interface 124 constructed in accordance with one embodiment of the invention. The user interface 124 includes a keyboard 126, a mouse 133, a touch screen 128, a series of soft keys 130 proximate the touch screen 128, a trackball 132, view position buttons 134, mode buttons 136 and control or operation keys 138. The soft keys 126 are assigned different functions on the touch screen 128 depending upon a selected examination mode, stage of examination and the like. The trackball 132 and keys 138 are used to control the display of images on the display 124 and control various options, for example, zoom, rotate, viewing mode, examination mode, etc. For example, the view position buttons 134 may change different views of the displayed image. Optionally, the view position buttons 134 may be implemented as touch areas 129 on the touch screen 128. As a further option, the size, position and orientation of the displayed image may be controlled partially or entirely by touch areas provided on the touch screen 128 and/or by the soft keys 130.

The user interface 124 also includes other controls, such as a save command/option 140 and a restore command/option 142 to save or restore certain image characteristics or changes to the displayed image. However, it should be noted that the various controls may be used to adjust or control different settings, display options, etc. For example, the user interface 124 may include a brightness control button 144 that allows a user to manually adjust screen brightness and a contrast control button 146 that allows a user to manually adjust screen contrast. For example, the brightness control button 144 may be used to enter a brightness control mode that allows a user to increase or decrease the brightness of the display 118 (shown in FIG. 2) using the touch areas 129 that may display up and down arrows to indicate brightness increase and brightness decrease, respectively. The contrast control button 146 likewise may be used to enter a contrast control mode that allows a user to increase or decrease the contrast of the display 118, again using the touch areas, where the arrows now increase and decrease screen contrast. The increasing or decreasing of the setting alternatively may be provided using other controls, such as moving the trackball 132 up/down or left/right. Any suitable controls may be provided to adjust the brightness or contrast, such as, roller wheels, dedicated toggles or buttons, etc.

In various embodiments, the functionalities of more than one probe are provided in a single probe body or acquisition component 52. One or more secondary heads (e.g., transducer 107) are added to a probe body (as discussed herein), forming a multi-headed probe 52 that provides a user with the ability to switch between a plurality of heads 106, 107 having distinct functions (e.g., heads having curved of linear arrays, 2D functions, and/or 3D functions). Multi-headed probe 52 facilitates rapid switching between transducers 106 and 107 by allowing a switch to be made with a simple rotation within a user's hand. The rotation can be of the multi-headed probe 52, itself, or of a multi-headed probe 52 inside a probe cover. Exam duration is reduced by eliminating or reducing the need for an exchange of probes during an exam and the requirement of a user to make movements between a patient examination area and a remote probe holder area. It should be noted that a window for the multi-headed probe 52 can be fixed (i.e., one window provided for each head, with the multi-headed probe fixed inside a probe cover) or adjustable, similar to the diaphragm of a photo camera (with one window for several heads, and the multi-headed probe rotatable within the probe cover).

Figure 4:
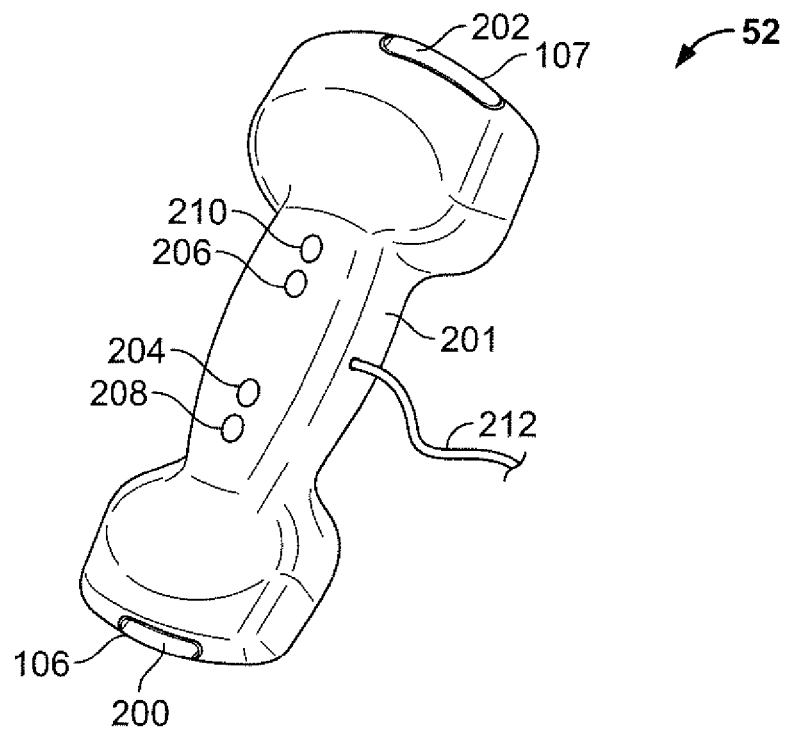
FIG. 4 is a drawing of a multi-headed probe constructed in accordance with an embodiment of the present invention.

FIG. 4 is a drawing of one embodiment of a multi-headed probe 52. Multi-headed probe 52 comprises two physically separated transducers 106 and 107, each having one or more transducer elements 104, not visible in FIG. 4. Each of the physically separated transducers 106 and 107 is covered by a separate window 200 and 202, respectively, with each window suitable for transmission of ultrasound emissions from transducer elements 104 into a patient's body and receiving echoes. For example, and not by way of limitation, windows 200 and 202 may comprise a clear acrylic resin, such as PLEXIGLAS®, which is pressed against a patient's body over a layer of sonogram gel. Also for example, and not by way of limitation, window 200 may cover a curved array of transducer elements 104 and window 202 may cover a linear array of transducer elements 104. In some embodiments of the present invention, multi-headed probe 52 is rotated until the desired transducer 106 or 107 is positioned proximate the patient, and the appropriate window 200 or 202 is pressed against the patient's body. In some embodiments of the present invention, to control whether transducer 106 or 107 is electrically activated, buttons 204 and 206, respectively, are provided on multi-headed probe 52. Buttons 204 and 206 can be located in a position that is easily reached by a user's hand while holding probe body 201. Furthermore, LEDs 208 and 210 (or another suitable type of visible or audible signaling device or devices) are provided in some embodiments to provide a visual indication of whether transducer 106 or 107, respectively, is activated.

To facilitate connection of transducers 106 and 107 with an imaging system 50, one embodiment of the present invention provides a single cable 212 for connection to imaging system 50 (shown in FIG. 1). Imaging system 50 is configured to receive a signal via cable 212 that depends upon whether button 204 or 206 is depressed. In response, imaging system 50 addresses transducers 106 and 107 (and/or respective elements 104), also via cable 212. If LEDs 208 and 210 are present, the appropriate LED is illuminated to indicate which transducer 106 or 107 is active.

In some embodiments, for additional ease in handling, cable 212 is very thin and comprises very thin wires (e.g., thin diameter or thin stranded wires) that are more flexible and less likely to tangle or obstruct during use. The cable 212 may be, for example, the type used for headphones of MP3 players, rather than the thick cable that is used with previously known single-head probes. In yet another embodiment of the present invention, a standard computer cable (such as a USB cable) is used as a connection between probe body 52 and imaging system 50 to facilitate the connection of multi-headed probe 52 to various types of personal computer-based imaging systems. In yet other embodiments, a battery (not shown) is provided in multi-headed probe 52. The battery may be a lithium ion rechargeable battery. The battery also powers a wireless transceiver (for example, and not by way of limitation, a BLUETOOTH® wireless transceiver) which takes the place of a wired connection between multi-headed probe 52 and imaging system 50, except that the battery rather than the wired connection provides power to operate either transducer 106 or 107 and LEDs 208 and 210, if present.

The present invention does not exclude embodiments in which a plurality of different connection modalities can be used between multi-headed probe 52 and imaging system 50. For example, multi-headed probe 52 can be provided with both a cable 212 and a BLUETOOTH wireless transceiver to facilitate connection of multi-headed probe 52 to a plurality of different imaging systems 50 and/or ease a transition between cabled and wireless instrumentation environments.

Figure 5:
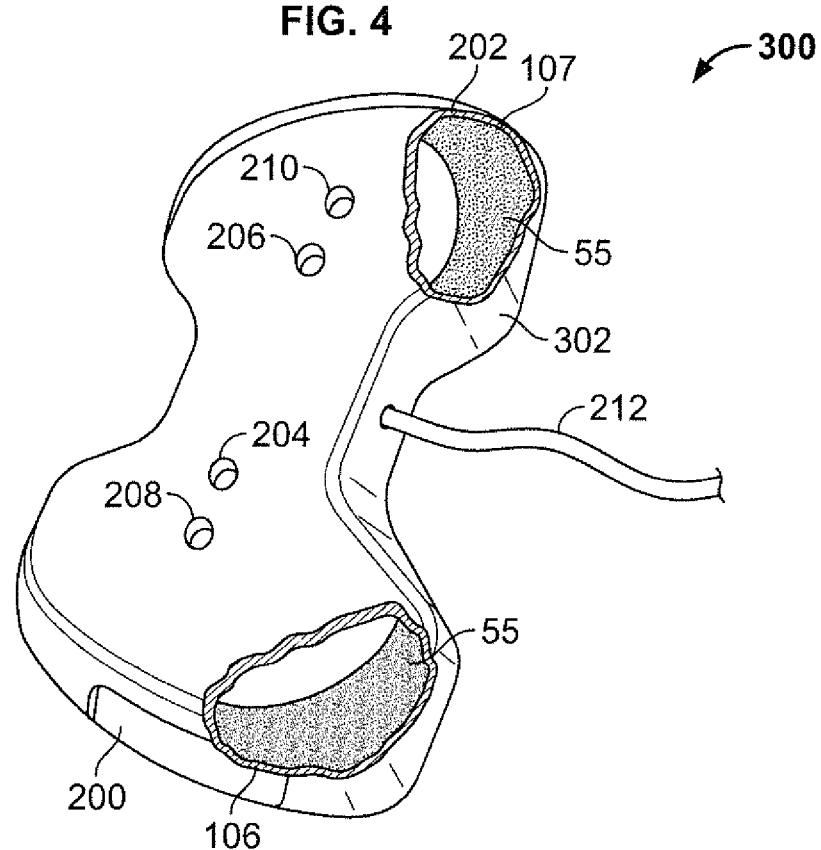
FIG. 5 is a cut-away drawing of a multi-headed probe case encasing a probe in another embodiment of the present invention.

FIG. 5 is a cut-away drawing of a multi-headed probe case 300 in another embodiment of the present invention. Probe case 300 comprises any suitable material such as a non-conductive plastic. Multi-headed probe 52 is encased in case 300 having windows (e.g., PLEXIGLAS windows) 302 and 304 that coincide with windows 200 and 202, respectively. Probe case 300 may also include an opening 302 through which a cable from the probe body 55 exits. Probe case 300 may also include other openings through which buttons 204 and 206 (or one or more equivalent switches by which the functions of buttons 204 and 206 may be accessed) may be pressed and/or an electrical connection with probe body 55 or imaging system 50 to external buttons for performing the same function on case 300. If openings are provided, they may be covered, for example, by a flexible rubber covering to prevent dust, dirt, and liquids from entering probe case 300 and/or probe body 55. If LEDs 208 and 210 are provided, the LEDs 208 and 210 may be provided on probe body 55 and made visible by additional clear windows on probe body 55. In another embodiment, LEDs 208 and 210 are on probe case 300 and are electrically connected to probe body 55 and/or imaging system 50.

Figure 6:
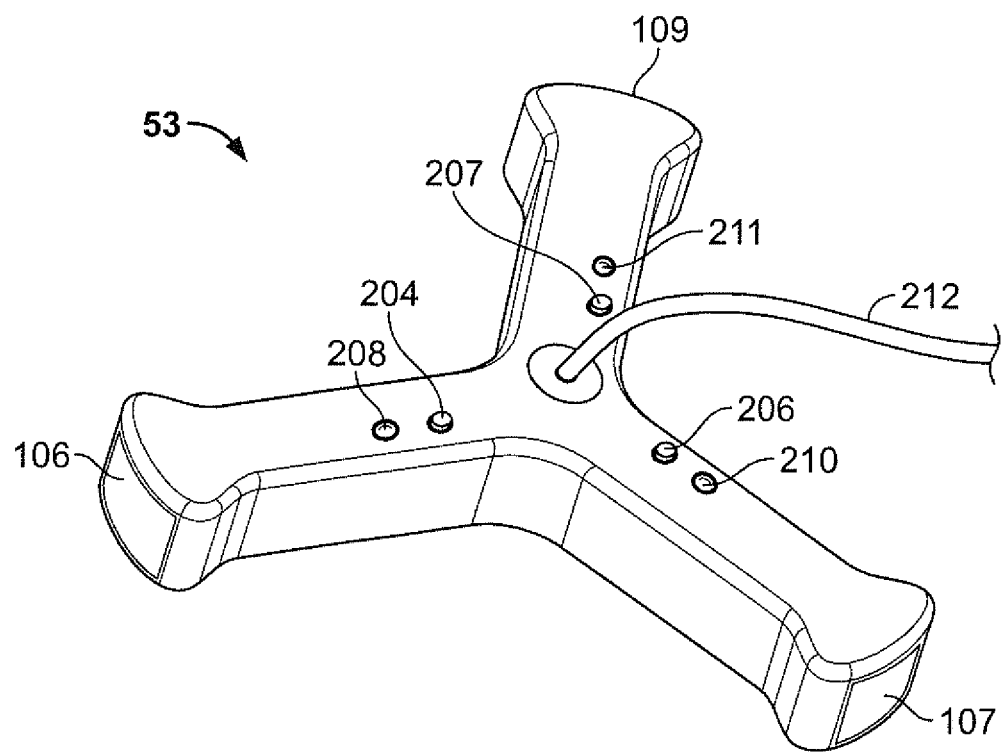
FIG. 6 is a drawing of a three-headed probe constructed in accordance with an embodiment of the present invention.

FIG. 6 is a drawing of a three-headed probe 53 similar to two-headed probe 52 of FIG. 5, but having three transducers 106, 107, and 109. To distinguish between a two-headed probe and a three-headed probe, the former is referred to as a multi-headed probe 52 and the latter as three-headed probe 53. Both types of probes, as well as probes with more than three heads, are considered to be multi-headed acquisition devices suitable for use with an imaging system 50. Each transducer 106, 107, and 109 includes a plurality of elements 104, not shown individually in FIG. 6. Three-headed probe 53 illustrates that embodiments of the present invention are not limited to probe bodies having only two transducer heads. Instead, embodiments of the present invention may include any number of heads, limited only by the size of the heads and the practicality of holding and using a probe large enough to hold the selected number of heads. Like numerals represent like parts as shown and described in FIGS. 4 and 5.

Figure 7:
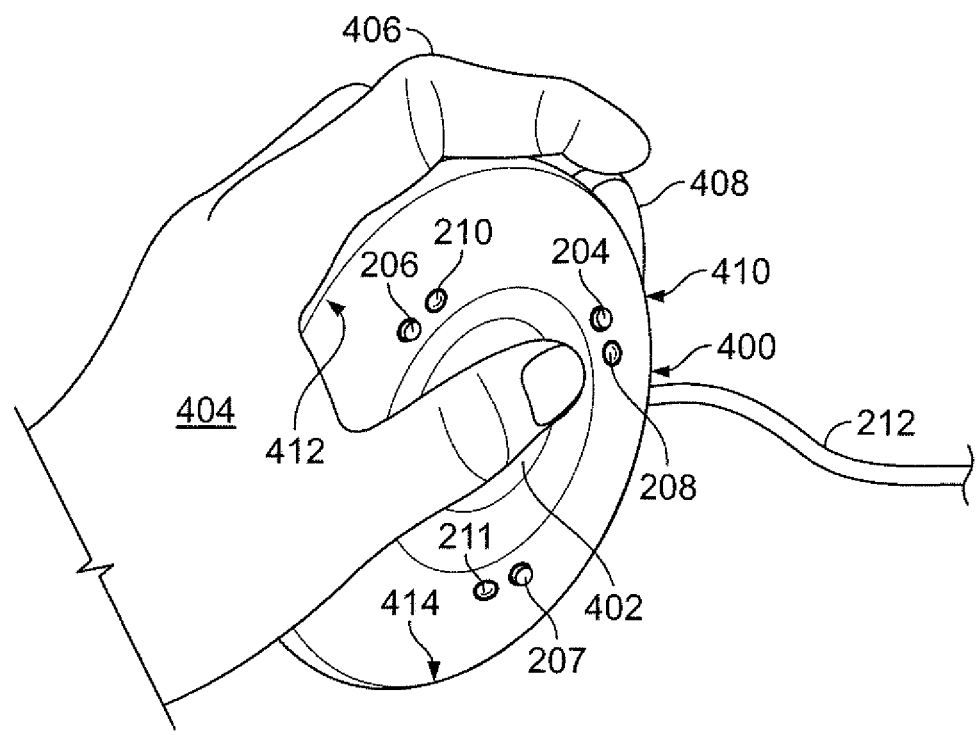
FIG. 7 is a drawing of a probe case having multiple windows and encasing a three-headed probe, constructed in accordance with another embodiment of the present invention.

FIG. 7 is a drawing of a probe case 400 encasing a multi-headed probe, for example, three-headed probe 53, in one embodiment of the present invention. Probe case 400, which comprises any suitable material such as a non-conductive plastic, is essentially disk-shaped. However, in some embodiments, case 400 includes a thumb rest or depression 402 to facilitate holding case 400 by providing a fixed and stable position for a user's hand 404. A thumb rest 402 may be provided in one or both sides of case 400. In the illustrated embodiment, an index finger 406 of the user rests on a button 408 that controls the transmission and capturing of information from the multi-headed probe inside case 400. Button 408 is provided to start acquisition and to freeze the acquisition of a picture acquired by an imaging apparatus 50. Button 408 is not required to be on case 400 (or on the probe, for that matter), however, as in some embodiments of the present invention that include a similar function, button 408 (or another suitable control) is positioned directly on imaging apparatus 50 (shown in FIG. 1) itself.

In one embodiment, case 400 has a number of windows appropriately positioned and equal to the number of transducers on the encased multi-headed probe, for example, three windows 410, 412, and 414 (not directly visible in FIG. 7, but indicated by position) for each of the three transducers 106, 107, and 109, respectively, of three-headed probe 53. Windows 410, 412, and 414 may be plastic or PLEXIGLAS windows, for example, positioned to coincide with transducers 106, 107, and 109, respectively.

To use this embodiment of the present invention, a sonograph gel is spread on a portion of patient's body where a sonogram is to be taken. An appropriate one of the three windows 410, 412, or 414, corresponding to a selected transducer 106, 107, or 109 having a desired shape, is pressed against the skin of the patient where the sonograph gel was spread. Case 400 is rocked back and forth on the patient's body as needed during the examination. When a differently shaped transducer is needed during the exam, the user rotates case 400 until the window for the desired transducer shape is in position to press against the skin of the patient.

Figure 8:
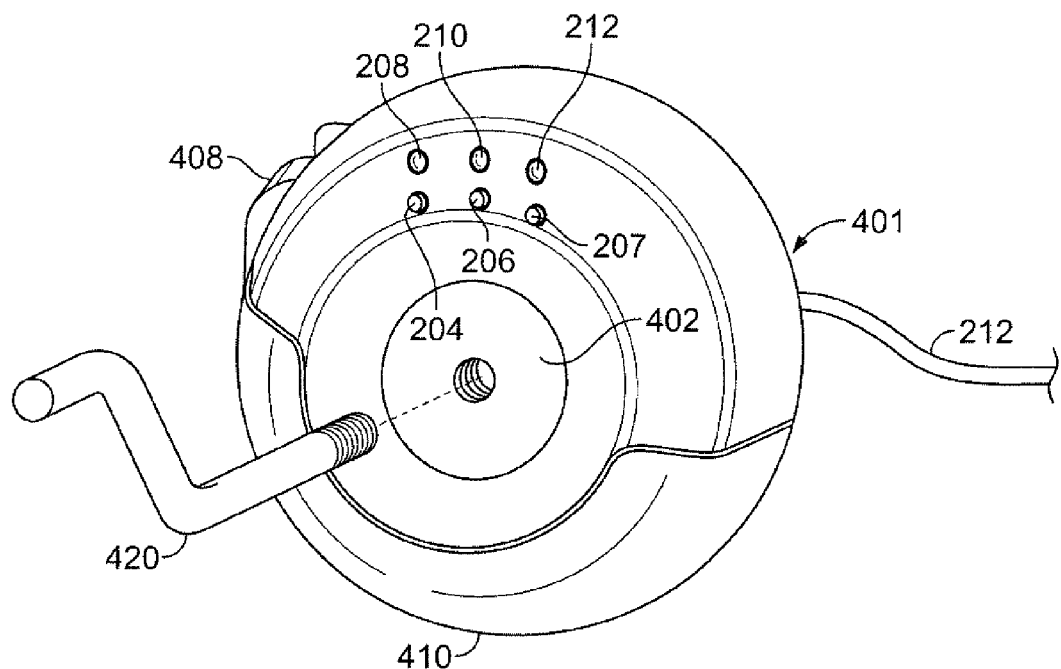
FIG. 8 is a drawing of a probe case having one window encasing a multi-headed probe constructed in accordance with another embodiment of the present invention.

FIG. 8 is a drawing of a probe case 401 encasing a multi-headed probe, for example, three-headed probe 53, in another configuration of the present invention. In this embodiment, case 401 has only one window 410, and probe 53 is rotated inside case 401 to position a selected transducer 106, 107, or 109 against window 410 inside probe case 401. A crank 420 or other suitable mechanical or electromechanical means (e.g., rotating knob) is used to rotate three-headed probe 53 inside probe case 401 in the illustrated embodiment.

In the embodiments illustrated in FIGS. 6, 7, and 8, buttons 204, 206, and 207 can be provided to activate a particular transducer 106, 107, or 109, and LEDs 208, 210, and 211 can be provided to indicate which transducer 106, 107, or 109, respectively, is active. The buttons and/or LEDs may be provided on case 400 or 401 or on probe 53 in a manner similar to that discussed above with respect to the embodiment illustrated in FIGS. 4 and/or 5 and the additional embodiments discussed in the text in connection therewith. Also, cable 212 may be a standard instrumentation cable or a thin cable, as discussed above, and/or probe 53 and imaging device 50 may communicate wirelessly, for example, via a BLUETOOTH connection, with space provided inside case 401 for a rechargeable or non-rechargeable battery.

Figure 9:
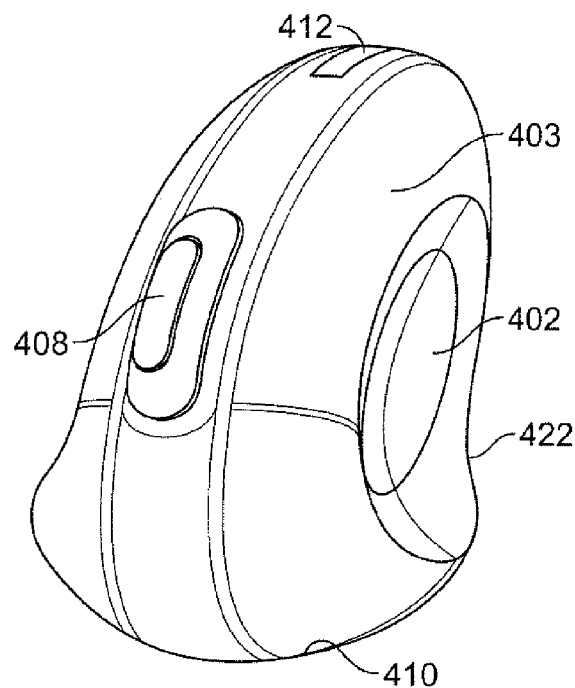
FIG. 9 is a drawing of a case for a two-headed probe constructed in accordance with an embodiment of the present invention wherein one of the probe heads is wider than the other.

A donut-like case 403 need not require that a three-headed probe 53 be encased therein. FIG. 9, for example, is an illustration of a case 403 suitable for a two-headed probe 52 wherein one of the probe heads is wider than the other. A widened portion 422 of case 400 is provided to accommodate the widened portion of the probe.

Figure 10:
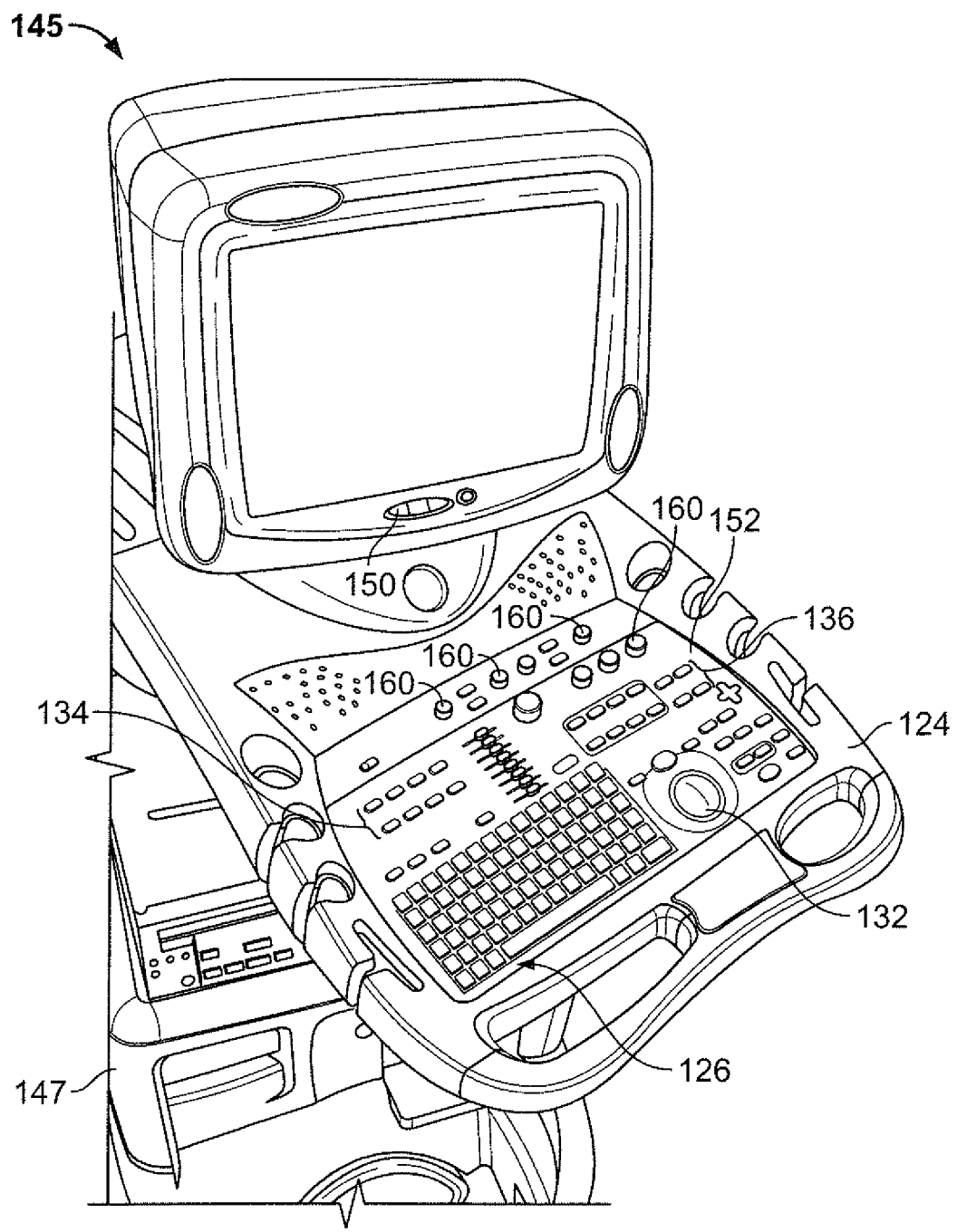
FIG. 10 is a drawing of a portable ultrasound imaging system constructed in accordance with an embodiment of the present invention.

Embodiments of the present invention may, for example, be implemented in an imaging system 50 such as a portable imaging system 145 (e.g., portable ultrasound system) provided on a movable base 147, as shown in FIG. 10. Manual screen adjustment controls 150 (e.g., brightness and contrast controls) are provided on the display 118. It should be understood that the display 118 may be separate or separable from the user interface 124. The user interface 124 may optionally be a touchscreen, allowing the user to select options by touching displayed graphics, icons, and the like.

The user interface 124 of FIG. 10 also includes other optional control buttons 152 that may be used to control the portable imaging system 145 as desired or needed, and/or as typically provided. The user interface 124 provides multiple interface options that the user may physically manipulate to interact with ultrasound data and other data that may be displayed, as well as to input information and set and change scanning parameters. The interface options may be used for specific inputs, programmable inputs, contextual inputs, and the like. Different types of physical controls are provided as different physical actions are more intuitive to the user for accomplishing specific system actions and thus achieving specific system responses.

For example, multi-function controls 160 are positioned proximate to the display 118 and provide a plurality of different physical states. For example, a single multi-function control may provide movement functionality of a clockwise/counterclockwise (CW/CCW) rotary, up/down toggle, left/right toggle, other positional toggle, and on/off or push-button, thus allowing a plurality of different states, such as eight or twelve different states. Different combinations are possible and are not limited to those discussed herein. Optionally, less than eight states may be provided, such as CW/CCW rotary functionality with at least two toggle positions, such as up/down toggle and/or left/right toggle. Optionally, at least two toggle positions may be provided with pushbutton functionality. The multi-function controls 160 may be configured, for example, as joystick rotary controls.

Figure 11:
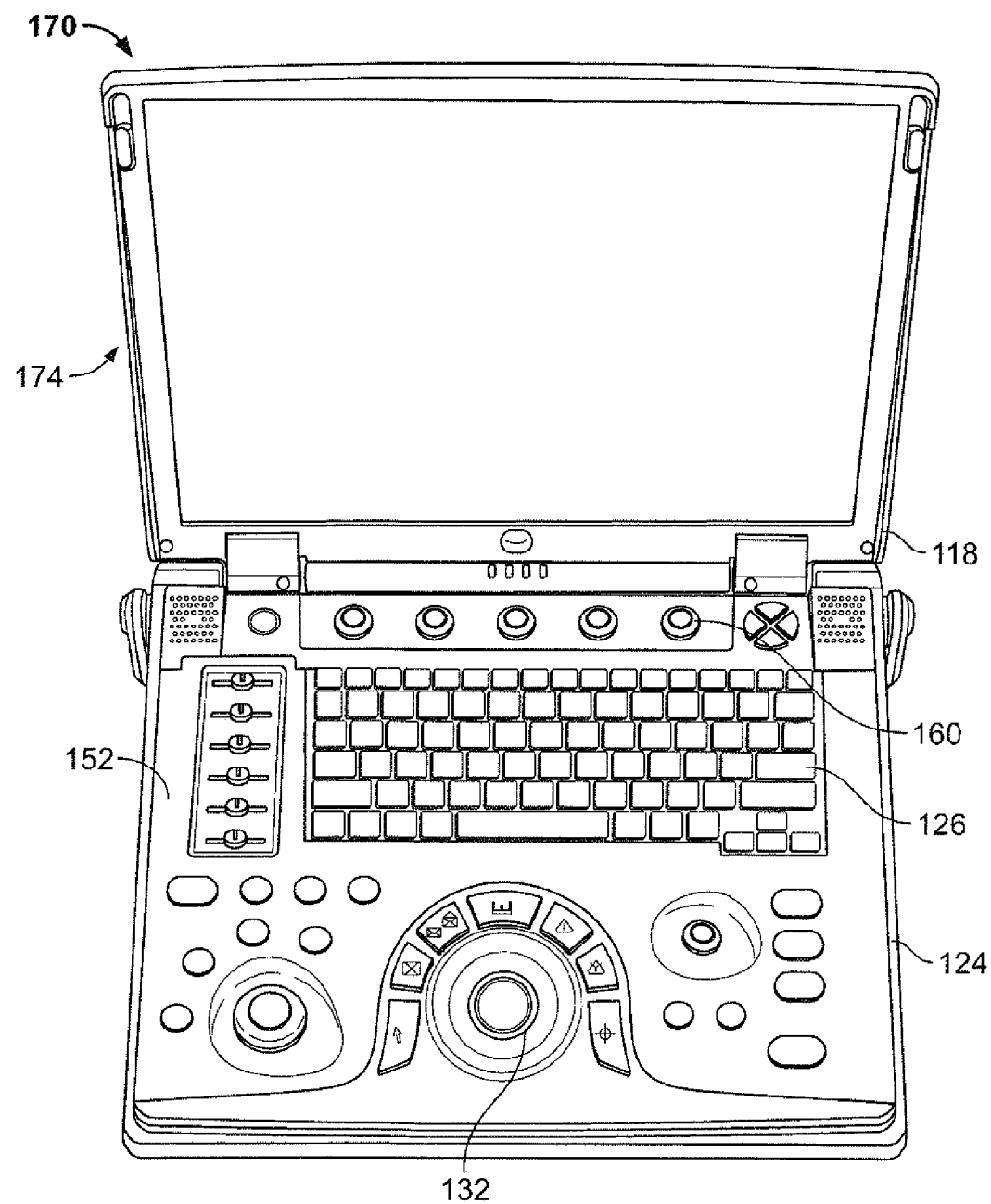
FIG. 11 is a drawing of a hand-carried ultrasound imaging system constructed in accordance with an embodiment of the present invention.

Embodiments of the present invention may also be provided in connection with an imaging system 50 such as a hand carried imaging system 170, as shown in FIG. 11, wherein the display 118 and user interface 124 form a single unit. The hand carried imaging system 170 may be, for example, a handheld or hand carried ultrasound imaging device, such as a miniaturized ultrasound system. As used herein, "miniaturized" means that the ultrasound system is a handheld or hand carried device or is configured to be carried in a person's hand, pocket, briefcase-sized case, or backpack. For example, the hand carried imaging system 170 may be a hand carried device having a size of a typical laptop computer, for instance, having dimensions of approximately 2.5 inches in depth, approximately 14 inches in width, and approximately 12 inches in height. The hand carried imaging system 170 may weigh about ten pounds.

Figure 12:
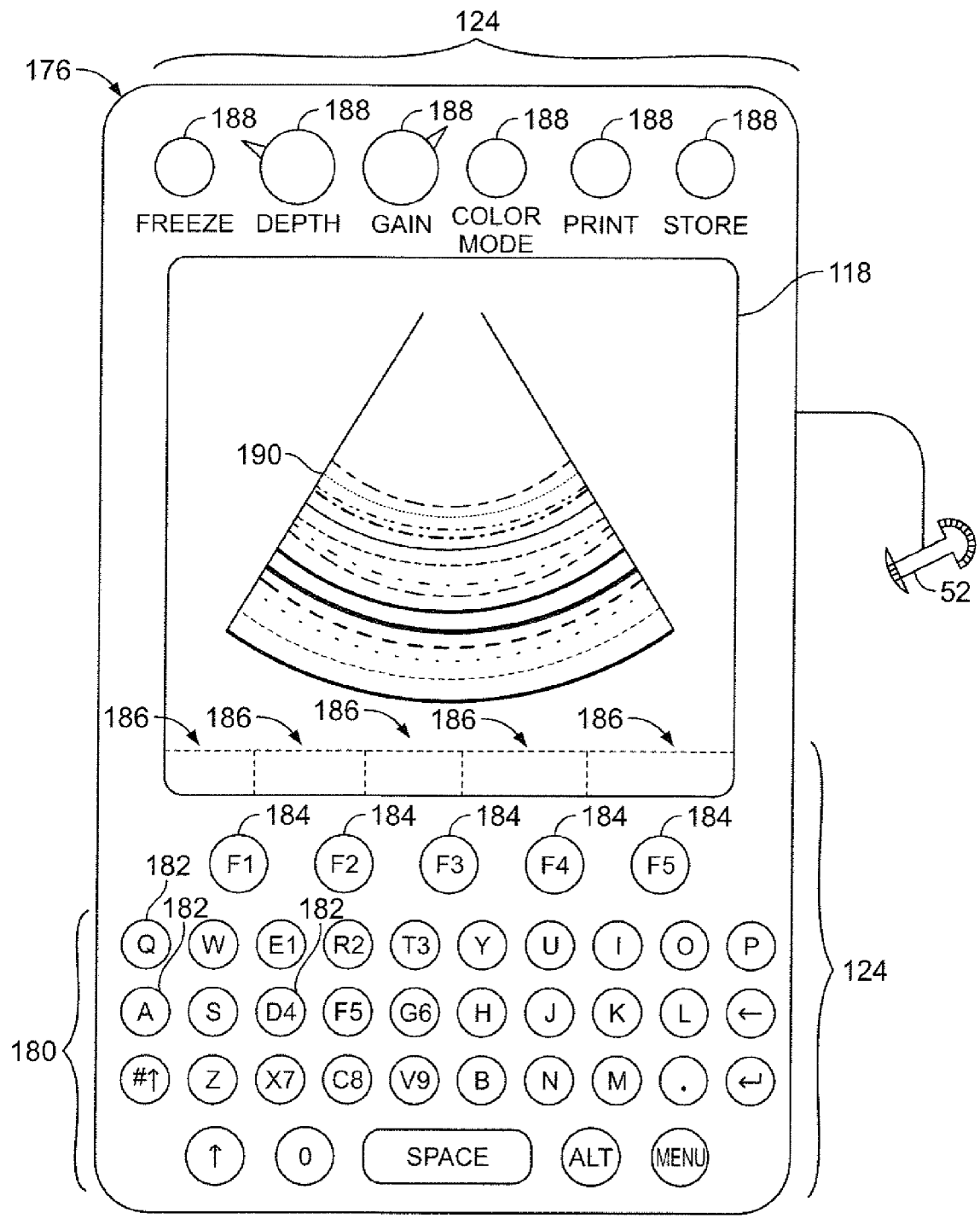
FIG. 12 is a drawing of a pocket-sized ultrasound imaging system constructed in accordance with an embodiment of the present invention.

Embodiments of the present invention may also be provided in connection with an imaging system 50 such as pocket-sized imaging system 176, as shown in FIG. 12, wherein the display 118 and user interface 124 form a single hand held unit. By way of example, the pocket-sized imaging system 176 may be a pocket-sized or hand-sized ultrasound system approximately 2 inches wide, approximately 4 inches in length, and approximately 0.5 inches in depth and weigh less than 3 ounces. The pocket-sized imaging system 176 generally includes the display 118, user interface 124, which may include a keyboard and an input/output (I/O) port for connection to an acquisition device, for example, a multi-headed ultrasound probe 52. The display 118 may be, for example, a 320×320 pixel color LCD display (on which a medical image 190 may be displayed). A typewriter-like keyboard 180 of buttons 182 may be included in the user interface 124. Multi-function controls 184 may each be assigned functions in accordance with the mode of system operation as previously discussed. As each of the multi-function controls 184 may be configured to provide a plurality of different physical actions, the mapping of system response to intuitive physical action may be improved without requiring additional space. Label display areas 186 associated with the multi-function controls 184 may be included as necessary on the display 118. The device may also have additional keys and/or controls 188 for special purpose functions, which may include, but are not limited to "freeze," "depth control," "gain control," "color-mode," "print," and "store."

Figure 13:
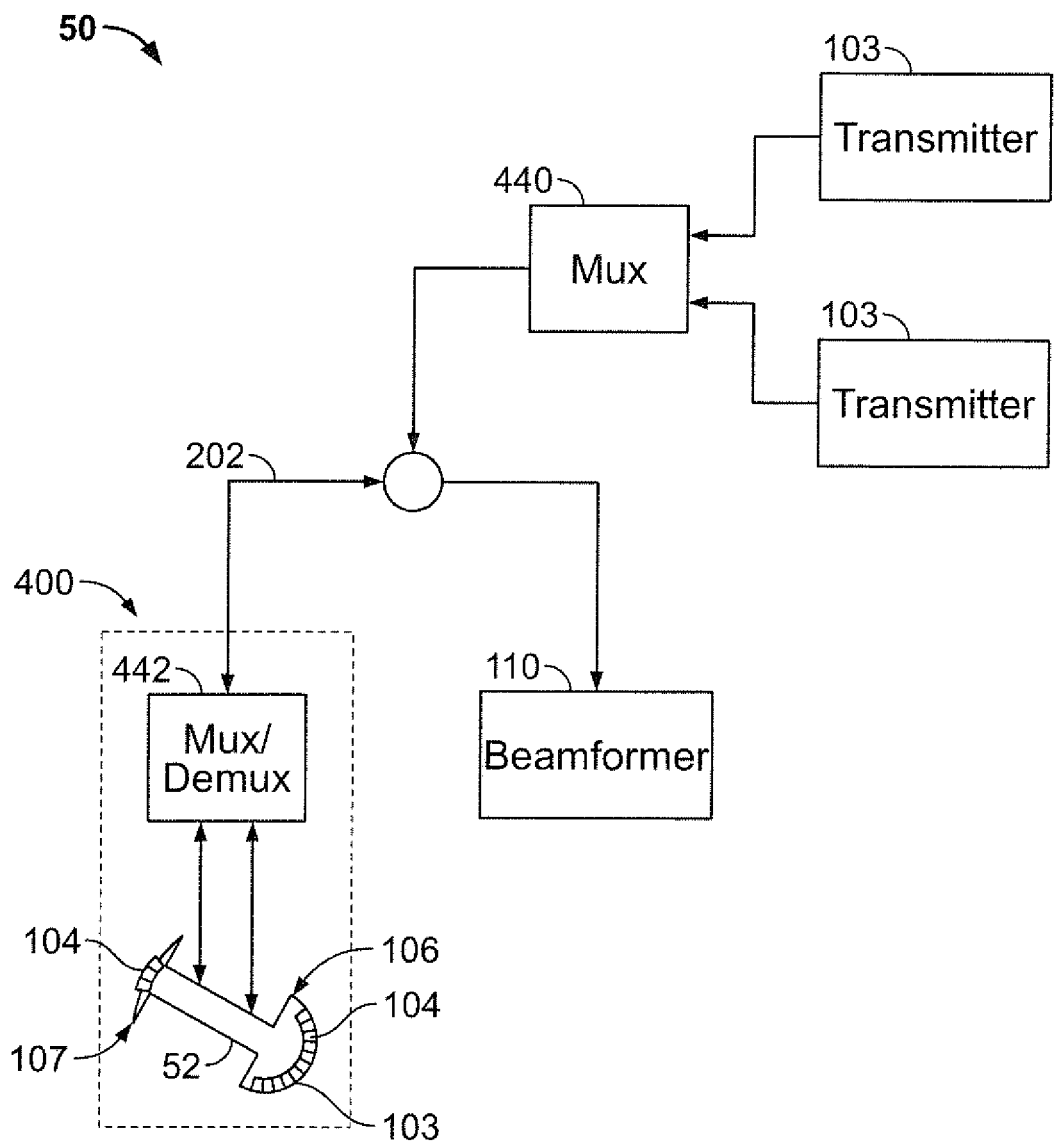
FIG. 13 is a schematic block diagram of a front end of an ultrasound imaging system constructed in accordance with an embodiment of the present invention including a multi-headed probe.

FIG. 13 is a block schematic diagram of an embodiment of a front end of an ultrasound imaging system of the present invention, including a multi-headed probe 52. In this particular embodiment, two transmitters 103 are provided, one for each transducer 106, 107, respectively, in probe 52, to pulse elements 104. The outputs of the transmitters are fed into a multiplexer 440, which is used to select which of transducers 106 or 107 is to be pulsed. The pulse output is sent through wire 212 to a multiplexer/demultiplexer 442 inside case 400, and from there, to the appropriate transducer 106 or 107 inside probe 52. Echoes are received by the same transducer and sent through multiplexer/demultiplexer 442 so that the output can be returned on the same cable 212 to a beamformer 110. Signals transmitted over cable 212 need not be digital signals, but may instead be analog signals, if analog to digital (A/D) converters and digital to analog (D/A) converters are provided in imaging apparatus 50 and/or probe 52 where circuitry requires such conversions.

Figure 14:
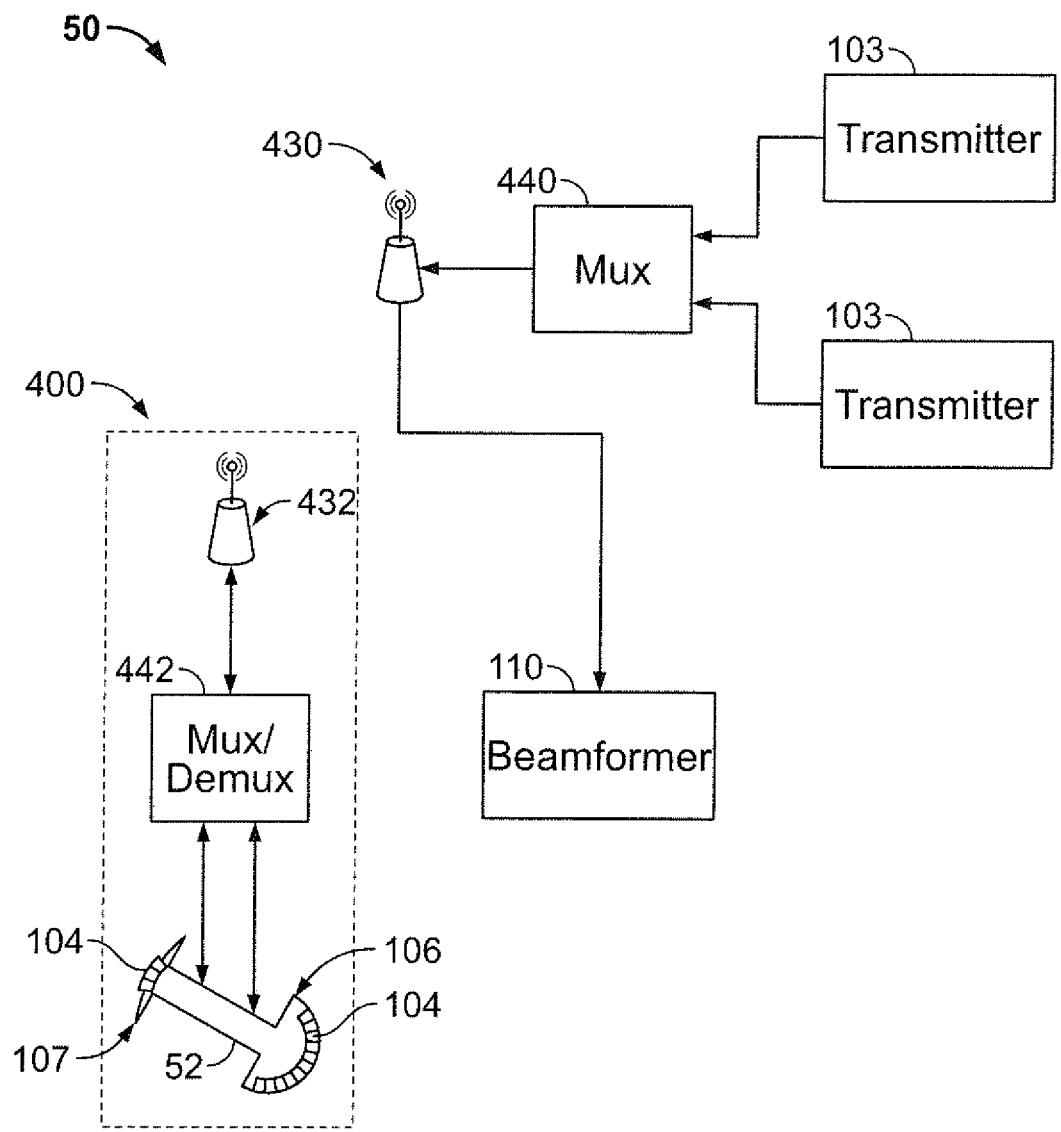
FIG. 14 is a schematic block diagram of a front end of an ultrasound imaging system constructed in accordance with an embodiment of the present invention having wireless functionality.

FIG. 14 is a block schematic diagram of a wireless embodiment of a front end of an ultrasound imaging system of the present invention. The embodiment shown in FIG. 14 is similar to that shown in FIG. 13, except that BLUETOOTH transceivers 430 and 432 are used to eliminate cable 212.

In some embodiments, elements 104 in transducer 106 and 107 form two separate address spaces and do not require the two transmitters and/or a multiplexer as shown in the embodiments of FIGS. 13 and 14.

It should be noted that the various embodiments may be implemented in connection with miniaturized imaging systems having different dimensions, weights, and power consumption. In some embodiments, the pocket-sized ultrasound system may provide the same functionality as the system 100 (shown in FIG. 1).

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

At least one technical effect of the various embodiments is to facilitate rapid switching between heads by allowing a switch of probe heads to be made with a simple rotation within user's hand. Multi-headed probe embodiments are cost effective by sharing a same electronic, connector, cable or wireless connection. Embodiments of the present invention are also time-efficient for sonographers by eliminating probe-exchange related actions during the examination procedure. Embodiments of the present invention also improve user comfort by reducing the risk of physical stress related to the repetition of probe-exchange related actions and some embodiments also provide a reduction of connectors and cables, thereby clearing space for operators to move their legs. Some configurations of the present invention are also fully portable, and/or permit a sonographer to acquire images using one or more types of probes (for example, and not by way of limitation, curved and linear arrays, 2D and 3D probes) directly at a patient bed in a hospital, or outside the hospital in an emergency situation. In some embodiments, one multi-headed probe replaces two or more probes during an ultrasound examination procedure, keeping the physical end-shape profile of a plurality of different types of probes and optimizing their positioning on patient, thereby preserving image quality.

It is to be understood that the above description is intended to be illustrative, and not restrictive. For example, the above-described embodiments (and/or aspects thereof) may be used in combination with each other to create new embodiments of the present invention, and not all features shown in the illustrated embodiments need necessarily be present to make use of the present invention. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A diagnostic imaging system comprising:
    an image acquisition component configured to provide image data;
    a processor configured to assemble images from said image data; and
    a display configured to display said images;
    wherein said image acquisition component comprises:
        a multi-headed probe having a single probe body having at least first and second windows in the single probe body; and
        at least first and second transducer heads in the single probe body and covered by the corresponding first and second windows for transmission of ultrasound waves and receiving echoes;
        wherein the probe body is elongated from a first end to an opposite second end with the first transducer head located at the first end of the probe body and the second transducer head located at the second end of the probe body, and
        wherein the first and second windows are located at fixed positions within the single probe body and are physically separated from one another such that, when one of the first or second windows is positioned against a patient at a region of interest (ROI), the other of the first or second windows is not positioned against the patient.

2. The imaging system of claim 1, wherein the first and second transducer heads are configured to provide distinct and different functions such that the first transducer head is active when the second transducer head is inactive.

3. The imaging system of claim 1, wherein the first and second transducer heads are different types of transducers.

4. The imaging system of claim 1, wherein the multi-headed probe is one of a two-headed probe or a three-headed probe.

5. The imaging system of claim 1, wherein the first transducer head includes a curved array of transducer elements and the second transducer head includes a linear array of transducer elements.

6. The imaging system of claim 1, wherein said probe body includes at least one button configured to be operated by a user and configured to switch an active one of the first or second transducer heads and an inactive one of the first or second transducer heads.

7. The imaging system of claim 1, wherein only one of the first or second transducer heads is active during a scanning session.

8. The imaging system of claim 1, wherein the probe body includes at least one of a visible or audible signaling device to provide at least one of a visual or audible indication, of which one of the first and second transducer heads is active.

9. The imaging system of claim 1, further comprising a probe case encasing the multi-headed probe, said probe case having case windows at opposed scanning ends of the probe case, the case windows coinciding with the first and second windows and transducer heads in the single probe body.

10. The imaging system of claim 1, wherein said multi-headed probe includes a transceiver configured to wirelessly communicate with at least one of said processor or said display.

11. The imaging system of claim 1, wherein said probe body includes at least one of a button configured to start and to freeze acquisition of an image, a button configured to select one of said first and second transducer heads on said probe for activation, or a visual or audible signaling device configured to signal which one of said transducers has been selected for activation.

12. The imaging system of claim 1, wherein the first and second transducer heads each perform a different one of a 2D function, 3D function, curved array function or linear array function.

13. The imaging system of claim 1, wherein said processor and said display are enclosed in a portable imaging system weighing about 10 pounds.

14. The imaging system of claim 1, wherein said processor and said display are enclosed in a portable imaging system weighing between about 10 pounds and about 3 ounces.

15. The imaging system of claim 1, wherein the display is a touch screen display.

16. The imaging system of claim 1, wherein the multi-headed probe wirelessly communicates with a portable imaging system.

17. The imaging system of claim 1, wherein the first and second transducer heads are fixed in position and orientation with respect to one another in the probe body.

18. The imaging system of claim 1, further comprising a standard computer cable, the image acquisition component in the multi-head probe configured to communicate with at least one of the processor or the display through the computer cable.

19. The imaging system of claim 1, wherein the first and second windows are located at the first and second ends of the single probe body, respectively.

20. The imaging system of claim 1, wherein a probe cable is joined to the single probe body at a location that is approximately equal distance between the first and second windows.

21. The imaging system of claim 20, wherein the at least first and second transducer heads consist of only two transducer heads.

22. A diagnostic ultrasound multi-head probe, comprising:
a single probe body having at least first and second windows in the single probe body; and
at least first and second transducer heads in the single probe body and covered by the corresponding first and second windows, respectively, for transmission of ultrasound waves and receiving echoes;
wherein the first and second windows are located at fixed positions within the single probe body and are physically separated from one another such that, when one of the first and second windows is positioned against a patient at a region of interest (ROI), the other of the first or second windows is not positioned against the patient,
wherein the probe body is elongated from a first end to an opposite second end with the first transducer head located at the first end of the probe body and the second transducer head located at the second end of the probe body.

23. The probe of claim 22, wherein the multi-headed probe is one of a two-headed probe or a three-headed probe.

24. The probe of claim 22, wherein the first transducer head includes a curved array of transducer elements and the second transducer head includes a linear array of transducer elements.

25. The probe of claim 22, wherein said probe body includes at least one button configured to be operated by a user and configured to switch an active one of the first or second transducer heads and an inactive one of the first or second transducer heads.

26. The probe of claim 22, wherein the probe body includes at least one of a visible or audible signaling device to provide at least one of a visual or audible indication of which one of the first and second transducer heads is active.

27. The probe of claim 22, wherein the first window and the first transducer head are located at the first end of the single probe body and the second window and the second transducer head are located at the second end of the single probe body.

28. The probe of claim 22, wherein the single probe body is elongated and a probe cable is joined to the single probe body at a location that is approximately equal distance between the first and second windows.

29. The probe of claim 22, wherein the at least first and second transducer heads consist of only two transducer heads.

* * * * *

EX PARTE REEXAMINATION CERTIFICATE (12634th)

United States Patent
Marteau et al.

(10) Number: US 9,532,768 C1
(45) Certificate Issued: Jun. 28, 2024

(54) MULTI-HEADED IMAGING PROBE AND IMAGING SYSTEM USING SAME

(71) Applicant: General Electric Company, Schenectady, NY (US)

(72) Inventors: Jean-Michel Marteau, Asnieres sur Seine (FR); Aurelie Roncaglioni, Bois d' Arcy (FR); Lionel Wodecki, Maisons-Alfort (FR)

(73) Assignee: GE PRECISION HEALTHCARE LLC, Waukesha, WI (US)

Reexamination Request:
No. 90/014,785, Jun. 25, 2021

Reexamination Certificate for:
Patent No.: 9,532,768
Issued: Jan. 3, 2017
Appl. No.: 13/913,124
Filed: Jun. 7, 2013

Related U.S. Application Data

(63) Continuation of application No. 13/281,283, filed on Oct. 25, 2011, now Pat. No. 8,480,591, which is a continuation of application No. 11/893,734, filed on Aug. 17, 2007, now Pat. No. 8,043,221.

(51) Int. Cl.
*A61B 8/00* (2006.01)
*A61B 8/08* (2006.01)

(52) U.S. Cl.
CPC .......... *A61B 8/4477* (2013.01); *A61B 8/4209* (2013.01); *A61B 8/4405* (2013.01); *A61B 8/4427* (2013.01); *A61B 8/4455* (2013.01); *A61B 8/4472* (2013.01); *A61B 8/463* (2013.01); *A61B 8/466* (2013.01); *A61B 8/469* (2013.01); *A61B 8/483* (2013.01); *A61B 8/54* (2013.01)

(58) Field of Classification Search
None
See application file for complete search history.

(56) References Cited

To view the complete listing of prior art documents cited during the proceeding for Reexamination Control Number 90/014,785, please refer to the USPTO's Patent Electronic System.

*Primary Examiner* — Glenn K Dawson

(57) ABSTRACT

A diagnostic imaging system is provided that includes an image acquisition component, a transmitter operatively coupled to the image acquisition component to transmit a signal therefrom, and a beamformer operatively coupled to the image acquisition component to receive image data therefrom. Also included is a processor configured to assemble images from the acquired image data and a display configured to display the images. The image acquisition component includes a multi-headed probe that has a plurality of transducers configured to permit a change of active transducers during an imaging session without a change of the image acquisition component.

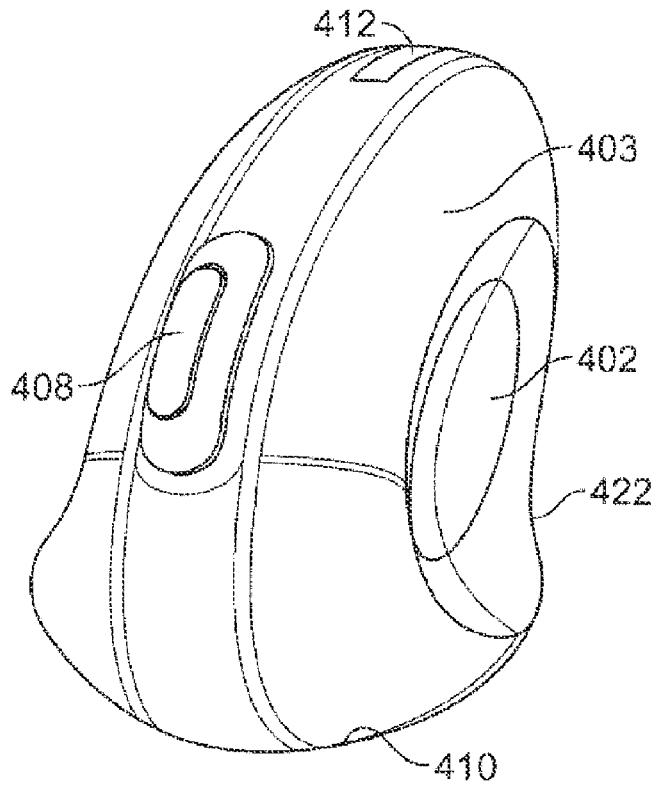

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-8 and 10-29 are cancelled.

Claim 9 is determined to be patentable as amended.

9. [The imaging system of claim 1, further comprising] *A diagnostic imaging system comprising:*
   an image acquisition component configured to provide image data;
   a processor configured to assemble images from said image data; and
   a display configured to display said images;
   wherein said image acquisition component comprises:
      a multi-headed probe having a single probe body having at least first and second windows in the single probe body;
      at least first and second transducer heads in the single probe body and covered by the corresponding first and second windows for transmission of ultrasound waves and receiving echoes;
   *wherein the probe body is elongated from a first end to an opposite second end with the first transducer head located at the first end of the probe body and the second transducer head located at the second end of the probe body, a first width of the probe body at the first end greater than a second width of the probe body at an intermediate portion of the probe body located between the first end and the second end, and*
   *wherein the first and second windows are located at fixed positions within the single probe body and are physically separated from one another such that, when one of the first or second windows is positioned against a patient at a region of interest (ROI), the other of the first or second windows is not positioned against the patient; and*
   a probe case encasing the multi-headed probe, said probe case having case windows at opposed scanning ends of the probe case, the case windows coinciding with the first and second windows and transducer heads in the single probe body.

* * * * *